United States Patent [19]

Ryder

[11] Patent Number: 4,787,656
[45] Date of Patent: Nov. 29, 1988

[54] CAPILLARY TUBING COUPLER

[75] Inventor: Bruce L. Ryder, Strasburg, Pa.

[73] Assignee: Hewlett-Packard Company, Palo Alto, Calif.

[21] Appl. No.: 746,614

[22] Filed: Jun. 19, 1985

[51] Int. Cl.⁴ ............................................. F16L 49/00
[52] U.S. Cl. ................................. 285/177; 285/911; 285/342; 285/353; 285/334.3; 55/386
[58] Field of Search ............... 285/342, 339, 354, 911, 285/334.1, 353, 177, 334.3; 55/386; 210/656, 198.2

[56] References Cited

U.S. PATENT DOCUMENTS

| 467,153 | 7/1943 | Muller | 285/342 |
|---|---|---|---|
| 823,944 | 6/1906 | Hart | 285/342 |
| 2,328,469 | 8/1943 | Laffly | 285/334.4 |
| 3,819,212 | 6/1974 | St. John et al. | 285/356 |
| 3,880,452 | 4/1975 | Fields | 285/177 |
| 4,083,702 | 4/1978 | Hartigan et al. | 55/67 |
| 4,304,425 | 12/1981 | Ikeda | 285/177 |
| 4,394,263 | 7/1983 | Dosch et al. | 55/386 |
| 4,529,230 | 7/1985 | Fatula | 285/341 |

Primary Examiner—Cornelius J. Husar
Assistant Examiner—Eric K. Nicholson
Attorney, Agent, or Firm—Donald N. Timbie

[57] ABSTRACT

A tubing coupling device constructed in accordance with this invention is comprised of a rigid body having cavity therein, an aperture communicating with the smaller end of said cavity and a tapered ferrule having an axial passageway that is aligned with the aperture. Means such as a nut that is in threaded engagement with the end of the rigid body opposite the aperture forces the ferrule into the cavity. The relative shapes and dimensions of the cavity and the ferrule are such that as the ferrule is forced into the cavity it is subjected to radial compression so as to attain intimate contact with the exterior surfaces of the end portions of tubes that are inside the ferrule.

5 Claims, 2 Drawing Sheets

CAPILLARY TUBING COUPLER

BACKGROUND OF THE INVENTION

In using chromatographs, whether gas, liquid or supercritical fluids are employed it is sometimes necessary to couple capillary tubes together. In an injection port, for example, the tube into which the syringe needle is thrust may be larger than the capillary column to which it is coupled. It may also be necessary to couple the output end of a separating column to a tube that is connected to a detector.

One significant disadvantage of presently known coupling devices is that they have a dead space communicating with the ends of tubes being coupled. A portion of the sample fluid emerging from the end of one tube quickly finds its way into the dead space but a relatively long time is required for it to enter the other tube. Therefore the concentration of the sample fluid emerging from the other end of the latter tube increases rapidly to a maximum value and then slowly decays to zero so as to cause a phenomenon known as tailing. As those skilled in the art are aware, the tail of one sample can enter a detector at the same time as the main portion of a succeeding sample fluid so as to make it difficult to separate the response to the detector to one sample from its response to the other.

Another significant disadvantage of presently known coupling devices is that the fluid flowing through the tubes can be degraded by contact with large areas of surfaces of the device other than the surfaces of the tubes.

BRIEF DESCRIPTION OF THE INVENTION

A tube coupling device constructed in accordance with this invention is comprised of a rigid body having a tapered cavity therein, an aperture communicating with the smaller end of said cavity and a tapered ferrule having an axial passageway that is aligned with the aperture. Means such as a nut that is in threaded engagement with the end of the rigid body opposite the aperture forces the ferrule into the cavity. The relative shapes and dimensions of the cavity and the ferrule are such that as the ferrule is forced into the cavity it is subjected to radial compression so as to attain intimate contact with the exterior surfaces of the end portions of tubes that are inside the ferrule.

In a preferred embodiment, the cavity and the outer surface of the ferrule both have the shape of a truncated cone, the diameter of the smaller end of the cavity is smaller than the diameter of the smaller end of the ferrule, and the angle of the taper of the cavity is greater than the angle of taper of the ferrule. In use, a given length of one tube is inserted through the aperture and into the cavity. When the ferrule is inserted into the cavity with its axis coinciding with that of the cavity and with the tapers sloping in the same direction, the outer edge of the smaller end of the ferrule first contacts the surface of the cavity at a given distance from the smaller end of the cavity. As the nut is tightened, the ferrule is radially compressed into intimate contact with the tube starting with the smaller end of the ferrule and proceeding toward its larger end. When the nut is partly tightened so that the first tube is firmly held, the second tube is inserted into the other end of the passageway of the ferrule until it abuts against the first tube. The nut is then further tightened so as to radially compress the ferrule into intimate contact with the junction of the tubes and then into intimate contact with the part of the second tube that is beyond the junction and within the ferrule. The second tube is then firmly gripped. At this point the smaller end of the ferrule should preferably not be in contact with the smaller end of the cavity. The fact that the ferrule grips the first tube before it grips the second makes it easier to control the point within the ferrule wherein the tubes abut.

By minimizing the dead space contact of the fluid with surfaces that could degrade the fluid is minimized.

By using inert material for the ferrule, the degrading of the fluid is further degraded. Ferrules made of polyimid have been found to work well for most fluids.

By virtue of the fact that the ends of the tubes are brought into contact, the flow of the fluid is undisturbed.

DETAILED DESCRIPTION OF THE INVENTION

Figure 2A:
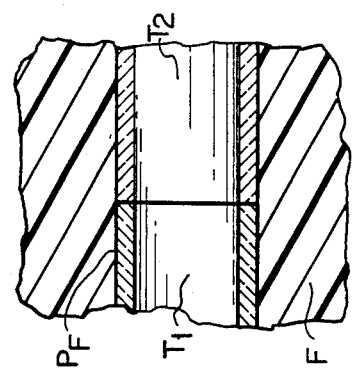
FIG. 2 is the same as FIG. 1 except that the ferrule has been forced into the cavity so as to form a seal about the abutting ends of the tubes.
Figure 1:
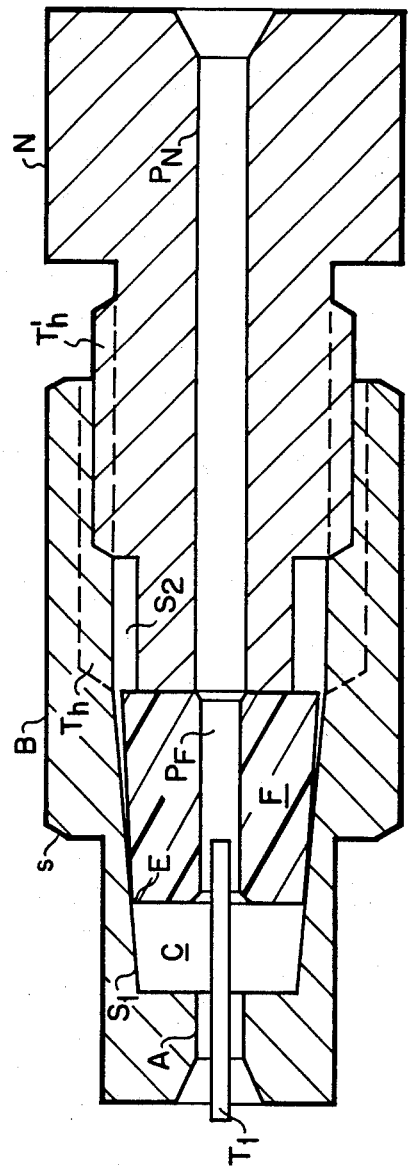
FIG. 1 is a cross section on the axial plane of a preferred form of a tube coupling device constructed in accordance with this invention taken at a point when the edge of the ferrule first makes contact with the wall of the cavity.

A preferred form of the tube coupling device of this invention is shown in FIG. 1. It is comprised of a rigid body B, a ferrule F and a nut N. The body B has a cavity C therein having two sections $S_1$ and $S_2$. The section $S_1$ is in the shape of a truncated right circular cone, and the section $S_2$ is in the shape of a cylinder. An aperture A through which a tube $T_1$, may be inserted communicates with the smaller end of $S_1$, and threads Th are formed on the inner surface of $S_2$.

Figure 1B:
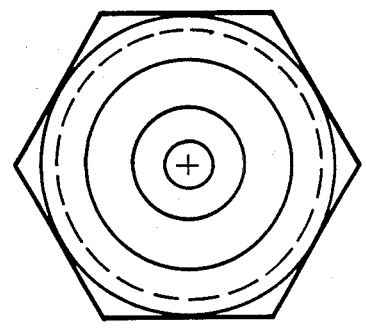
FIG. 1B is an axial view of the end of the rigid body into which the nut is threaded.
Figure 1C:
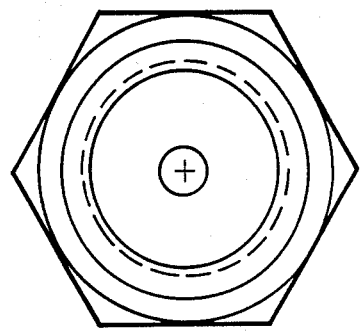
FIG. 1C is an axial view of the nut from its threaded end.
Figure 1A:
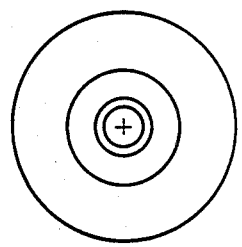
FIG. 1A is an axial view of the smaller end of the ferrule.

The nut N has an axial passageway Pn and threads Th' that mesh with the threads Th. FIGS. 1A, 1B and 1C respectively show the axial view of the smaller end of the ferrule F, the axial view of the threaded end of the rigid body B and the axial view of the threaded end of the nut N.

The ferrule F is in the form of a truncated right circular cone having an axial passageway Pf. In an actual device, the taper of the external surface of the ferrule F is about one degree less than the taper of the inner surface of the section $S_1$ but the difference has been exaggerated for explanatory purposes. The diameter of the smaller end of the ferrule F is slightly larger than the diameter of the smaller end of the section $S_1$.

FIG. 1 illustrates the relative positions of the rigid body B, the nut N and the ferrule F at the start of the coupling procedure in which the corner E of the ferrule F just touches the inner surface of $S_1$, its larger end is even with the larger end of $S_1$ and in contact with the nut N. Because of the fact that the diameter of the passageway Pf is larger than the outer diameter of the tube $T_1$, the latter must be held in position with its end at the axial position of a shoulder s until the nut N is turned. When this occurs the ferrule F is forced deeper into the conically shaped section $S_1$ of the cavity C so as to place the smaller end of the ferrule F in radial compression. This establishes a firm contact between the smaller end of the ferrule F and the outside of the tube $T_1$. At this point, a tube $T_2$ is inserted through the passageway Pn on the nut N until it bears against the end of the tube $T_1$. As the nut N is further tightened, intimate contact between the ferrule F and the tube $T_1$ advances to the ends of $T_1$ and $T_2$ and beyond so as to form a seal shown in FIG. 2. Tests have shown that practically no tailing is caused by the coupling device described. The dead space, if any, is between the ends of the tubes $T_1$ and $T_2$ and this can be practically eliminated if the ends of the tubes are perpendicular to their axes and flat.

Figure 2:
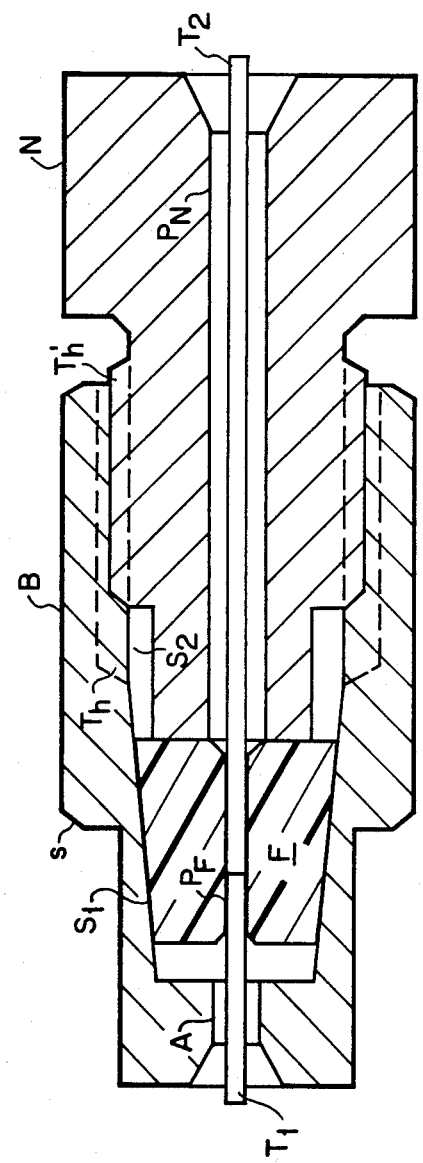

Although it is of little consequence, note that the end of $T_1$ is moved toward the aperture A after initial firm contact is made between $T_1$ and the ferrule F so that it ends up to the left of the shoulder s as shown in FIG. 2.

Because the section $S_1$ and the ferrule F are conical and therefore have circular cross sections, the radial compression of the ferrule F is the same at all points around its axis. Whereas this is preferable because it establishes a uniformly firm contact at all points around the outside of the tube $T_1$, it would be possible for the section $S_1$ and the ferrule F to have cross sections that are other than circular e.g., square or triangular, and in fact the cross sections could be different. It is important that the cross section and dimensions be such as to cause radial compression of the ferrule F.

Although it would require greater torque to turn the nut N, it would be possible to secure a seal with little or no dead space by making the angle of the tape of the ferrule F greater than the angle of taper of the section $S_1$ of the cavity C so that the first contact between the ferrule F and $S_1$ would be at the larger end of the ferrule F and would proceed toward the smaller end of F as the nut N is tightened. In such event the tube $T_2$ would be inserted first, and firm contact between it and the ferrule F would proceed toward the small end of the ferrule F as the nut N is tightened.

It would also be possible for the tapers of $S_1$ and F to be the same, but this would make it difficult to known when the ends of the tubes are in contact.

Figure 3B:
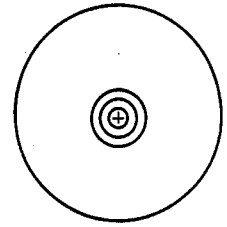
FIG. 3B is an axial view of the larger end of the ferrule of FIG. 3.
Figure 3:
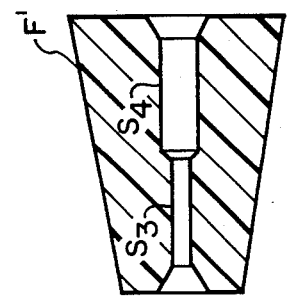
FIG. 3 is a cross section in a plane including the axis of a ferrule having an axial passageway with sections of different diameters joined by a tapered section.
Figure 3A:
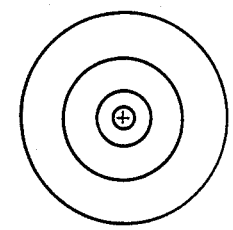
FIG. 3A is an axial view of the smaller end of the ferrule of FIG. 3.

FIG. 3 illustrates a cross-section taken through the axis of a ferrule F' having an axial passageway that has successive sections $S_3$ and $S_4$ of different diameters joined by a tapered section so as to couple tubes of different diameters with little or no dead space. The sections $S_3$ and $S_4$ are formed by a tapered section so as to minimize flow disturbance. FIG. 3A is an axial view of the smaller end of the ferrule F' and FIG. 3B is an axial view of the larger end of the ferrule F'. The radial compression is brought about in the same way described above so as to provide a tight fit between the ferrule F' and the tubes that may be inserted in the passageways $S_3$ and $S_4$.

What is claimed is:

1. A device for coupling the ends of two tubes in abutting relationship comprising:
    a body,
    means defining a cavity in said body having a tapered surface,
    means defining an aperture in said body communicating with said cavity,
    a ferrule made of material that is more compressible than the material from which said body is made, said ferrule having an exterior tapered surface that is positioned in said cavity with the tapers sloping in the same direction,
    means defining a passageway extending through said ferrule that communicates with said aperture, and
    means coupled to said body that can be operated so as to force the tapered surface of said ferrule into said cavity in such a manner that the only radial compression of the ferrule occurs the portion bounded by its tapered surface.

2. A device as set forth in claim 1 wherein said tapered surfaces are frusto-conical and have different angles of taper.

3. A device as set forth in claim 1 wherein the passageway in said ferrule has two sections of different cross sectional areas within the tapered surface.

4. A device as set forth in claim 1 further comprising
    a first tube, said first tube being inserted into one end of said passageway in said ferrule, and
    a second tube, said second tube being inserted into the other end of said passageway in said the ends of said first and second tubes meeting within the tapered surface.

5. A method of coupling the ends of two tubes in abutting relationship comprising:
    bring a frusto-conical surface of a ferrule having a passageway extending along the axis of the surface into initial contact with a frusto-conical surface forming a cavity,
    inserting one tube into one end of said passageway so that its end lies in the portion of the ferrule that is bounded by its frusto-conical surface,
    forcing the ferrule farther into said cavity so as to radially compress the ferrule into gripping contact with said one tube,
    inserting another tube into the other end of said passageway until its end abuts the end of the first tube, and
    forcing the ferrule still further into the cavity so as to radially compress the portion of the ferrule bounded by said frusto-conical surface into contact with the abutting ends of said tubes.

* * * * *